United States Patent [19]

Matsushita et al.

[11] Patent Number: 4,515,008
[45] Date of Patent: May 7, 1985

[54] POLYMERIZATION RATE DETECTION METHOD

[75] Inventors: Nobuo Matsushita; Tokinobu Furukawa, both of Kudamatsu; Tetsuo Shintani, Hikari; Tomoaki Sumitani; Chikao Oda, both of Kudamatsu, all of Japan

[73] Assignee: Hitachi, Ltd., Tokyo, Japan

[21] Appl. No.: 503,349

[22] Filed: Jun. 10, 1983

[30] Foreign Application Priority Data

Jun. 16, 1982 [JP] Japan .................. 57-102053

[51] Int. Cl.$^3$ ............................................. G01N 33/44
[52] U.S. Cl. ............................................ 73/53; 436/34
[58] Field of Search .................... 73/53, 61 R, 61.1 R; 436/34

[56] References Cited

U.S. PATENT DOCUMENTS

| | | | |
|---|---|---|---|
| 2,590,436 | 3/1952 | Luten, Jr. ........................ | 436/34 X |
| 3,477,819 | 11/1969 | Fernald et al. ...................... | 436/34 |
| 3,578,404 | 5/1971 | Walles et al. ........................ | 436/34 |
| 3,746,509 | 7/1973 | Koskan ................................. | 436/34 |

FOREIGN PATENT DOCUMENTS

| | | | |
|---|---|---|---|
| 6610286 | 1/1967 | Netherlands ......................... | 436/34 |
| 238876 | 3/1969 | U.S.S.R. .............................. | 436/34 |

Primary Examiner—Howard A. Birmiel
Assistant Examiner—Joseph W. Roskos
Attorney, Agent, or Firm—Antonelli, Terry & Wands

[57] ABSTRACT

A method for detecting a polymerization rate, wherein a polymer composition in a polymerization reaction process is sampled out and can be measured, and is separated into a volatile component and a non-volatile component, and the polymerization rate of the polymer composition is determined using the measured amount of the volatile component and/or non-volatile component, and also possibly the measured amount of the sample. Such method is best suited for detecting the rate of polymerization of polymer compositions. This enables proper quality control of the polymer composition in the polymerization reaction process.

11 Claims, 1 Drawing Figure

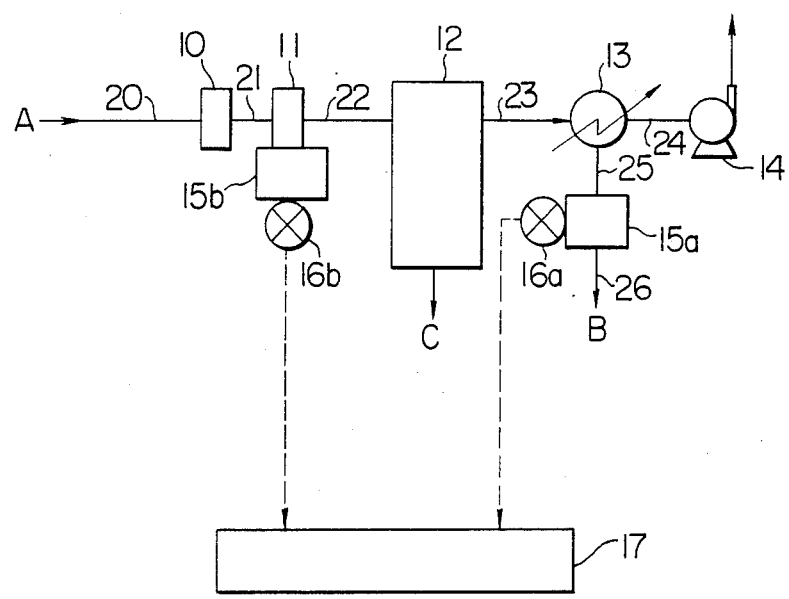

POLYMERIZATION RATE DETECTION METHOD

BACKGROUND OF THE INVENTION

This invention relates to a method for detecting the rate of polymerization. More specifically, it relates to such a polymerization rate detection method which is best suited for detecting the polymerization rate of a polymer composition in a polymerization reaction process using any kind of polymerization such as bulk polymerization, solution polymerization, emulsion polymerization, suspension polymerization, etc.

In a polymerization reaction process of a polymer composition, it is important for proper quality control of the composition to detect the polymerization rate of the polymer composition in the course of the polymerization reaction process in a short time and with high accuracy.

Heretofore, the polymerization rate of a polymer composition in a polymerization reaction process has been detected by applying an interrelation existing between polymerization rate and viscosity of polymer composition under certain constant conditions (such as measuring temperature, polymerization temperature, shear rate in measurement of viscosity, etc.). In such a conventional method, the viscosity of the polymer composition to be examined is first measured and the polymerization rate of the polymer composition is detected from a diagram representing the polymerization rate-viscosity relation of polymer compositions which diagram has been obtained from the experimentally obtained data.

Such a detection method, though capable of detecting the polymerization rate of a polymer composition in a polymerization reaction process in a short time, had the following disadvantages.

(1) As it is generally difficult to keep constant such conditions as measuring temperature and shear rate in measurement of viscosity of polymer composition, errors tend to appear in determination of polymerization rate of polymer composition from the polymerization rate-viscosity diagram on the basis of the measured viscosity. This makes impossible high-accuracy detection of the polymerization rate of the polymer composition in a polymerization reaction process, disenabling proper quality control of the polymer composition throughout the reaction process.

(2) A change in any of the conditions such as measuring temperature, polymerization temperature, shear rate in measurement of viscosity, etc., causes a corresponding change in the relation between polymerization rate and viscosity of polymer composition. Therefore, when drawing up a polymerization rate-viscosity diagram with such possible changes in mind, a vast accumulation of data on the relation between polymerization rate and viscosity of polymer compositions changeful with diversified combinations of said variable conditions is necessitated, for which a great deal of time and expense are required.

An analytical method by use of a gas analyzer (gas chromatography) is known for detecting the polymerization rate of a polymer composition with higher accuracy. This method, however, is rather complicated in its process, which essentially comprises a sample dissolving step in which a sample of the polymer composition to be analyzed is dissolved in a solvent to form a sample solution, a sample solution measuring step in which a small amount of said sample solution is quantified accurately and supplied into the analyzer, and an analysis step where the sample solution in the analyzer is gasified and passed through a filler-packed column and the efflux rate at the column outlet is measured and output as a calibration curve. The objective polymerization rate is detected by passing these steps, so that this method is incapable of short-time detection of the polymerization rate of a polymer composition in a polymerization reaction process and is therefore unable to ensure proper quality control of the polymer composition throughout the reaction process.

SUMMARY OF THE INVENTION

An object of this invention is to provide a method for detecting the rate of polymerization of a polymer composition in a polymerization reaction process in a short time and with high accuracy, thereby enabling proper quality control of the polymer composition throughout the reaction process employing any kind of polymerization such as bulk polymerization, solution polymerization, emulsion polymerization, suspension polymerization, etc.

This invention provides a process for detecting a polymerization rate of a polymer composition during a polymerization reaction process in a short time and with good accuracy, according to which method a predetermined amount of a polymer composition, during a polymerization reaction process, is sampled out, and can be measured then, the polymer composition taken out is separated into volatile component and non-volatile component; and then the amount of said volatile component or non-volatile component, or both the volatile and non-volatile components, is measured, and the polymerization rate of the polymer composition is determined from the measured amount of said volatile and/or non-volatile component, and possibly the measured amount of the polymer composition. This method allows short-time and high-accuracy detection of the polymerization rate of a polymer composition in a polymerization reaction process.

BRIEF DESCRIPTION OF THE DRAWING

The drawing is a flow sheet illustrating one example of polymerization rate detecting apparatus used for practising this invention.

DETAILED DESCRIPTION OF PREFERRED EMBODIMENTS

An embodiment of this invention will be described below with reference to the accompanying drawing.

In the drawing, the polymerization rate detecting system is connected by a conduit 20 to an element, such as a polymerization reactor (not shown), in a polymerization reaction process, said conduit 20 being connected at its other end to an inlet of a constant-rate feeder 10. An outlet of said feeder 10 is connected by a conduit 21 to an inlet of a determined-amount sample extractor, for example, a gear pump 11 whose rotating speed regulates the flow rate. Said gear pump 11, in turn, has its outlet connected by a conduit 22 to a polymer composition feed port of a separator 12 in which the polymer composition is separated into a volatile component (monomer(s) in the case of bulk polymerization and monomer(s) and a medium such as solvent, emulsifier, dispersant, etc., in the case of polymerization other than bulk polymerization) and a non-volatile component (a polymer). The outlet (volatile component discharging port in the shown embodiment) of said separator 12 is connected to an inlet of a condenser 13 by a conduit 23, said condenser 13 being in turn connected by a conduit 24 to a vacuum pump 14 which operates to keep the operating pressure in the separator 12 below the vapor pressure of the volatile component and above the vapor pressure of the non-volatile component. The outlet of said condenser 13, from which the volatile component liquefied therein is discharged out, is connected by a conduit 25 to an inlet of a measuring device 15a whose outlet connects to a conduit 26. The gear pump 11 is provided with another measuring device 15b. A measured value output means, for example, an analog-digital (A/D) converter 16a (16b) is connected to each of said measuring devices 15a and 15b. Said both A/D converters 16a and 16b are connected to a polymerization rate indicator or display 17. Said both measuring devices 15a and 15b may be constituted, for example, from a system in which the extracted sample is quantified from the flow rate measured by a flowmeter, or a system in which the sample is first stored in a tank and then the weight change of the liquid is measured by using a load cell or other suitable means, or a system in which the change of liquid level is measured by a level gauge. Any other suitable system may be employed. For the polymerization rate display 17, there may be employed any suitable device which is capable of memorizing the measured values and also has the determined polymerization rate operating and displaying functions. The separator 12 may be a thinfilm evaporator which can be quickly renewed in its surface and also has volatilizing capacity of up to several hundreds ppm in a short time.

In operation of the above-described detecting system of this invention, first a polymer composition in a polymerization reaction process, in this case a polymer composition in a polymerization reactor, is supplied from the polymerization reactor into the constant-rate feeder 10 through conduit 20 and futher passed through conduit 21 into the gear pump 11 whereby a determined amount of said composition is extracted and the sample of polymer composition A precisely measured by the measuring device 15b. The measured value is converted by the A/D converter 16b and input to the polymerization rate display 17. Then, the sample of polymer composition is supplied into the separator 12 from the gear pump 11, through conduit 22. This sample of polymer composition A is separated into a volatile component B and a non-volatile component C in a short time in the separator 12 which is operated under a pressure which is kept below the vapor pressure of the volatile component B and above the vapor pressure of the non-volatile component C by the vacuum pump 14. The non-volatile component C is discharged out of the separator 12 without being subjected to measurement. On the other hand, the volatile component B is supplied from the separator 12 through conduit 23 into the condenser 13 where the volatile component B is entirely condensed and liquefied in a short time. The liquefied volatile component B is measured by the measuring device 15a and then discharged out of the system via conduit 26. The measured value of the volatile component B is converted by the A/D converter 16a and input to the display 17. After the measured values of both volatile component B and polymer composition A have thus been converted by the respective A/D converters 16a and 16b and input to the display means 17, the measured values are operated by using the following equations (1) to (7) in said display means 17 and the thus determined polymerization rate of the polymer composition in the polymerization reactor is indicated on the display 17.

That is, the rate of polymerization can be obtained by the following equations:

$$\text{Rate of polymerization (\%)} = \frac{\text{Flow rate of polymer}}{\left(\begin{array}{c}\text{Flow rate}\\\text{of monomer}\end{array}\right) + \left(\begin{array}{c}\text{Flow rate}\\\text{of polymer}\end{array}\right)} \times 100 \quad (1)$$

$$= \left[1 - \frac{\text{Flow rate of monomer}}{\left(\begin{array}{c}\text{Flow rate}\\\text{of monomer}\end{array}\right) + \left(\begin{array}{c}\text{Flow rate}\\\text{of polymer}\end{array}\right)}\right] \times 100 \quad (2)$$

In bulk polymerization, there is the following relationship:

$$\left(\begin{array}{c}\text{Flow rate}\\\text{of polymer}\\\text{composition } (A)\end{array}\right) = \left(\begin{array}{c}\text{Flow rate of}\\\text{monomer } (B)\end{array}\right) + \left(\begin{array}{c}\text{Flow rate of}\\\text{polymer } (C)\end{array}\right) \quad (3)$$

In polymerization other than bulk polymerization, there is the following relationship:

$$\left(\begin{array}{c}\text{Flow rate}\\\text{of polymer}\\\text{composition } (A)\end{array}\right) = \left(\begin{array}{c}\text{Flow rate of}\\\text{monomer } (B_1)\end{array}\right) + \left(\begin{array}{c}\text{Flow rate of}\\\text{polymer } (C)\end{array}\right) + \left(\begin{array}{c}\text{Flow rate of}\\\text{a medium } (B_2)^*\end{array}\right) \quad (4)$$

*Flow rate of a medium ($B_2$) is known from the flow rate of the medium charged.

Using the above-mentioned equations, the rate of polymerization can be obtained as follows:

(a) Bulk polymerization

Measuring either the flow rate (e.g. kg/hr) of polymer composition (A) and that of monomer (i.e. volatile component) (B) or the flow rate of polymer (i.e. non-volatile component) (C), the rate of polymerization can be obtained by the equation (1) or (2).

(b) Polymerization other than bulk polymerization

Although the flow rate of a medium ($B_2$) is included in the flow rate of polymer composition (A) and the flow rate of volatile component (B), there are the following relationships since the flow rate of a medium ($B_2$) is a known value:

$$\left(\begin{array}{c}\text{Flow rate of}\\\text{monomer } (B_1)\end{array}\right) + \left(\begin{array}{c}\text{Flow rate of}\\\text{polymer } (C)\end{array}\right) = \left(\begin{array}{c}\text{Flow rate}\\\text{of polymer}\\\text{composition } (A)\end{array}\right) - \left(\begin{array}{c}\text{Flow rate of}\\\text{medium } (B_2)\end{array}\right) \quad (5)$$

$$\left(\begin{array}{c}\text{Flow rate of}\\\text{monomer } (B_1)\end{array}\right) = \left(\begin{array}{c}\text{Flow rate}\\\text{of volatile}\\\text{component } (B)\end{array}\right) - \left(\begin{array}{c}\text{Flow rate of}\\\text{medium } (B_2)\end{array}\right) \quad (6)$$

$$\left(\begin{array}{c}\text{Flow rate of}\\\text{polymer } (C)\end{array}\right) = \left(\begin{array}{c}\text{Flow rate of}\\\text{non-volatile}\\\text{component } (C)\end{array}\right) = \quad (7)$$

$$\left(\begin{array}{c}\text{Flow rate}\\ \text{of polymer}\\ \text{compositon }(A)\end{array}\right) - \left(\begin{array}{c}\text{Flow rate}\\ \text{of volatile}\\ \text{component }(B)\end{array}\right)$$

Therefore, when either the flow rate of polymer composition (A) and that of volatile component (B) or the flow rate of non-volatile component (C) is measured as in the case of bulk polymerization, the flow rate of monomer ($B_1$) and that of polymer (C) can be obtained from the equations (5), (6) and (7), and thus the rate of polymerization can be obtained by the equation (1).

The method for detecting the rate of polymerization according to this invention can effectively be used in the polymerization of such monomers as styrene, ethylene, vinyl chloride, propylene, methyl methacrylate, and the like.

According to the polymerization rate detection method described hereinabove as an embodiment of this invention, no much time is required for the separation of the polymer composition supplied from a polymerization reactor into volatile component and non-volatile component and for the display of the measured polymerization rate, so that the intended detection of the polymerization rate can be accomplished in a short time. Also because the direct ratio of the amount of a quantified sample of the polymer composition to the amount of the volatile component separated from the sample of composition is used for the determination, it is possible to detect the polymerization rate with very high accuracy, thus enabling always proper quality control of said polymer composition in the reactor. Further, since the polymerization rate can be detected from the amount of the sampled polymer composition and the amount of the volatile component separated from the sample as said above, there is no need of drawing up a polymerization rate-viscosity diagram of polymer compositions as in the prior art nor is there any necessity for collecting voluminous data on said polymerization rate-viscosity relation which are required for drawing up said diagram.

In the above-described embodiment of this invention, the amount of the volatile component is measured after it has been condensed and liquefied, but it is also possible to quantify said volatile component without condensing and liquefying it but keeping it in a gaseous state and measuring its flow rate. Further, in the above-shown embodiment, the polymerization rate is detected by measuring the volatile component separated from a sample of polymer composition, but it is possible to detect the polymerization rate be measuring the non-volatile component separated from said sample of polymer composition simultaneously with the volatile component. Moreover, it is also possible to separate the volatile component and non-volatile component, to measure the amounts of the volatile and non-volatile components thus separated, and to detect the polymerization rate of the polymer composition using the measured amounts of the volatile component and the non-volatile component, e.g., without measuring the total sample. Thus, the polymer composition in the polymerization reaction process may be directly sampled out into the separator from the reaction process line.

According to the method of this invention, as described above, a polymer composition in a polymerization reaction process is sampled out and the amount thereof can be measured, and the sample is separated into volatile component and non-volatile component and the amount of such volatile component and/or non-volatile component is measured, and the polymerization rate is detected using the measured amounts of the volatile component and/or non-volatile component so that, according to this method, the polymerization rate of a polymer composition in a polymerization reaction process can be detected in a short time and with high accuracy, allowing proper quality control of any polymer composition in a polymerization reaction process.

What is claimed is:

1. A process for detecting rate of polymerization, which comprises:
   a step of taking out a predetermined amount of a polymer composition from a polymerization reaction process and measuring the amount thereof,
   a step of separating the polymer composition thus measured into a volatile component and a non-volatile component,
   a step of measuring the amount of the separated volatile component, and
   a step of calculating the rate of polymerization of the polymer composition by using the measured amount of the polymer composition and the measured amount of the volatile component.

2. A process according to claim 1, wherein the volatile component separated from the polymer composition is condensed and liquefied to measure the amount thereof.

3. A process according to claim 1, wherein the amount of the separated volatile component is measured in the state of gas.

4. A process according to claim 1, wherein the separation of the polymer composition into the volatile component and the non-volatile component is carried out under a pressure not higher than the vapor pressure of the volatile component and not lower than the vapor pressure of the non-volatile component.

5. A process according to claim 1, wherein the polymerization reaction process is a process for polymerizing a monomer selected from the group consisting of styrene, ethylene, vinyl chloride, propylene, and methyl methacrylate.

6. A process for detecting rate of polymerization, which comprises:
   a step of taking out a predetermined amount of a polymer composition from a polymerization reaction process and measuring the amount thereof,
   a step of separating the measured polymer composition into a volatile component and a non-volatile component,
   a step of measuring the amount of the separated non-volatile component, and
   a step of calculating the rate of polymerization of the polymer composition by using the measured amount of the polymer composition and the measured amount of the non-volatile component.

7. A process according to claim 6, wherein the separation of the polymer composition into the volatile component and the non-volatile component is carried out under a pressure not higher than the vapor pressure of the volatile component and not lower than the vapor pressure of the non-volatile component.

8. A process according to claim 6, wherein the polymerization reaction process is a process for polymerizing a monomer selected from the group consisting of styrene, ethylene, vinyl chloride, propylene, and methyl methacrylate.

9. A process for determining rate of polymerization, which comprises:
- a step of taking out a predetermined amount of a polymer composition from a polymerization reaction process,
- a step of separating the polymer composition into a volatile component and a non-volatile component,
- a step of measuring the amounts of the separated volatile component and the separated non-volatile component, and
- a step of calculating the rate of polymerization of the polymer composition by using the measured amount of the volatile component and the measured amount of the non-volatile component.

10. A process according to claim 9, wherein the separation of the polymer composition into the volatile component and the non-volatile component is carried out under a pressure not higher than the vapor pressure of the volatile component and not lower than the vapor pressure of the non-volatile component.

11. A process according to claim 9, wherein the polymerization reaction process is a process for polymerizing a monomer selected from the group consisting of styrene, ethylene, vinyl chloride, propylene, and methyl methacrylate.

* * * * *